United States Patent [19]

Bernstein et al.

[11] Patent Number: 5,648,061

[45] Date of Patent: Jul. 15, 1997

[54] IN VIVO AND IN VITRO MODEL OF CUTANEOUS PHOTOAGING

[75] Inventors: Eric Bernstein, Wynnewood; Jouni Uitto, Gladwyne, both of Pa.

[73] Assignee: Thomas Jefferson University, Philadelphia, Pa.

[21] Appl. No.: 449,826

[22] Filed: May 24, 1995

[51] Int. Cl.$^6$ .............................. A61K 49/00; C12Q 1/02
[52] U.S. Cl. ...................... 424/9.2; 435/29; 435/172.3; 800/2; 935/59
[58] Field of Search ..................... 800/2, DIG. 1; 435/172.3, 240.2, 29; 424/9.2; 935/59

[56] References Cited

PUBLICATIONS

EF Bernstein et al (1993) J Investigative Dermatology 101:464.
VM Kahari et al (1990) J Biol Chem. 265: 9485–9490.
S Hsu-Wong et al (1992) Clinical Research 40: 188A.
Berger et al., "Experimental Elastosis Induced by Chronic Ultraviolet Exposure", Arch. Dermatol. Res. 1980, 269:39–49.
Bernstein et al., "Enhanced Elastin and Fibrillin Gene Expression in Chronically Photodamaged Skin", J. Invest. Dermatol. 1994, 103:182–186.
Bissett et al., "An Animal Model of Solar-Aged Skin: Histological, Physical, and Visible Changes in UV-Irradiated Hairless Mouse Skin", Photochem. Photobiol. 1987, 46:367–376.
Bissett et al., "Wavelength Dependence of Histological, Physical, and Visible Changes in Chronically UV-Irradiaed Hairless House Skin", Photochem. Photobiol. 1989, 50:763–769.
Chen et al., "Immunochemistry of Elastotic Material in Sun-Damaged Skin", J. Invest. Dermatol. 1986, 87:334–337.
Dahlback et al., "Fibrillin Immunoreactive Fibers Constitute a Unique Network in the Human Dermis: Immunohistochemical Comparison of the Distributions of Fibrillin, Vitronectin, Amyloid P Component, and Orcein Stainable Structures in Normal Skin and Elastosis", J. Invest. Dermatol. 1990, 94:284–291.
Frances, C. and Robert L., "Elastin and Elastic Fibers in Normal and Pathologic Skin", Int. J. Dermatol. 1984, 23:166–179.
Hsu-Wong et al., "Tissue-specific and Developmentally Regulated Expression of Human Elastin Promoter Activity in Transgenic Mice", J. Biol. Chem. 1994, 269:18072–18075.
Kligman, L.H., Aging and the Skin. Raven Press, New York, 1989, pp. 331–346.

Kligman, L.H., "Intensification of Ultraviolet–induced Dermal Damage by Infrared Radiation", Arch. Dermatol. Res. 1982, 272:229–238.
Kligman et al., "Prevention of Ultraviolet Damage to the Dermis of Hairless Mice by Sunscreens", J. Invest. Dermatol. 1982, 78:181–189.
Kligman et al., "The Contributions of UVA and UVB to Connective Tissue Damage in Hairless Mice", J. Invest. Dermatol. 1985, 84:272–276.
Kligman, L.H. and Sayre, R.M., "An Action Spectrum for Ultraviolet Induced Elastosis in Hairless Mice: Quantification of Elastosis by Image Analysis", Photochem. Photobiol. 1991, 53:237–242.
Mera et al., "Elastic fibres in normal and sun–damaged skin: an immunohistochemical study", Br. J. Dermatol. 1987, 117:21–27.
Montagna et al., "Histology of sun–damaged skin", J. Am. Acad. Dermatol. 1989, 21:907–918.
Moran, M. and Granstein, R.D., "Experimental Photoaging in C3H/HeN, C3H/HeJ, and Balb/c Mice: Comparison of Changes in Extracellular Matrix Components and Mast Cell Numbers", J. Invest. Dermatol. 1994, 103:797–800.
Nakamura, K. and Johnson, W.C., "Ultraviolet Light Induced Connective Tissue Changes in Rat Skin: A Histopathologic and Histochemical Study", J. Invest. Dermatol. 1968, 51:253–258.
Poulsen et al., "Dermal elastosis in hairless mice after UV–B and UV–A applied simultaneously, separately or sequentially", Br. J. Dermatol. 1984, 110:531–538.
Sams et al., "The Experimental Production of Elastosis with Ultraviolet Light", J. Invest. Dermatol. 1964, 43:467–471.
Taylor et al., "Photoaging/photodamage and photoprotection", J. Am. Acad. Dermatol. 1990, 221:1–15.
Warren et al., "Age, sunlight and facial skin: A histologic and quantitative study", J. Am. Acad. Dermatol. 1991, 25:751–760.
Wulf et al., "Narrow–band UV radiation and induction of dermal elastosis and skin cancer", Photodermatology 1989, 6:44–51.
Zimmerman et al., "Versican Is Expressed in the Proliferating Zone in the Epidermis and in Association with the Elastic Network of the Dermis", J. Cell. Biol. 1994, 124:817–825.

Primary Examiner—Bruce R. Campell
Attorney, Agent, or Firm—Law Offices of Jane Massey Licata

[57] ABSTRACT

A transgenic mouse capable of expressing human elastin promoter is provided. Mouse fibroblast cultures derived from this transgenic mouse are also provided. In addition methods of identifying compounds capable of inhibiting cutaneous photodamage with this transgenic mouse or fibroblast cultures derived from these mice are provided.

2 Claims, No Drawings

IN VIVO AND IN VITRO MODEL OF CUTANEOUS PHOTOAGING

BACKGROUND OF THE INVENTION

Cutaneous aging results from both intrinsic chronological aging and extrinsic sun-exposure. Montagna et al., *J. Am. Acad. Dermatol.* 1989, 21:907–918; Kligman, L. H., Aging and the Skin. Raven Press, New York, 1989, pp. 331–346; Taylor et al., *J. Am. Acad. Dermatol.* 1990, 221:1–15. The majority of changes associated with an aged appearance result from chronic sun-damage. Warren et al., *J. Am. Acad. Dermatol.* 1991, 25:751–760; Frances, C. and Robert, L., *Int. J. Dermatol.* 1984, 23:166–179. Dramatic alterations of the superficial dermis accompany the deep wrinkles and laxity common in photoaged skin. The major histopathologic alteration of photoaged skin is the accumulation of material which, on routine histopathologic examination, has the staining characteristics of elastin and is, thus, termed solar elastosis. Immunohistochemical staining has shown the poorly-formed fibers comprising solar elastosis to be composed of elastin (Chen et al., *J. Invest. Dermatol.* 1986, 87:334–337; Mera et al., *Br. J. Dermatol.* 1987, 117:21–27) fibrillin (Chen et al., *J. Invest. Dermatol.* 1986, 87:334–337; Dahlback et al., *J. Invest. Dermatol.* 1990, 94:284–291; Bernstein et al., *J. Invest. Dermatol.* 1994, 103:182–186) and versican, the normal components of elastic fibers (Zimmerman et al., *J. Cell. Biol.* 1994, 124:817–825). A coordinate increase in elastin, fibrillin and versican mRNAs has been demonstrated in fibroblasts derived from photodamaged skin, as compared to fibroblasts derived from normal skin from the same individuals. Bernstein et al., *J. Invest. Dermatol.* 1994, 103:182–186. Elevated elastin mRNA levels in sun-damaged skin result from enhanced elastin promoter activity, as shown by transient transfections of fibroblasts with a DNA construct composed of the human elastin promoter linked to the chloramphenicol acetyltransferase (CAT) reporter gene. Bernstein et al., *J. Invest. Dermatol.* 1994, 103:182–186.

A transgenic mouse line which expresses the human elastin promoter/CAT construct has now been developed to further study the role of elastin promoter activation in cutaneous photoaging. These mice express human elastin promoter activity in a tissue-specific and developmentally regulated manner. Promoter activity can be studied in this model as a function of small increases in ultraviolet radiation, demonstrating the sensitivity of the assay. In addition quantitative data can be obtained after only a single exposure to ultraviolet radiation. This transgenic mouse and fibroblasts derived from this mouse are useful as in vivo and in vitro models to study cutaneous photoaging and in the identification of agents which may protect against photodamage.

SUMMARY OF THE INVENTION

An object of the present invention is to provide a transgenic mouse capable of expressing human elastin promoter.

Another object of the present invention is to provide mouse fibroblast cultures derived from a transgenic mouse capable of expressing human elastin promoter.

Method of identifying compounds capable of inhibiting cutaneous photodamage using either the transgenic mouse or fibroblasts derived from these mice are also provided.

DETAILED DESCRIPTION OF THE INVENTION

Profound changes take place in the superficial dermis as a result of chronic sun-exposure. The major alteration is the deposition of massive amounts of abnormal elastic material, termed solar elastosis. It has been shown that solar elastosis is accompanied by elevations in elastin and fibrillin mRNAs and elastin promoter activity. A transgenic mouse model useful as both an in vivo and in vitro model for studying cutaneous photoaging, and for testing compounds that may inhibit cutaneous photodamage has now been developed. Using this transgenic mouse line, which expresses the human elastin promoter linked to a chloramphenicol acetyltransferase (CAT) reporter gene in a tissue-specific and developmentally regulated manner, it is now possible to investigate the effects of ultraviolet A (UVA) and ultraviolet B (UVB) on human elastin promoter activity in vivo and in vitro.

In mice a single dose of UVB (491.4 mJ/cm$^2$) resulted in up to an 8.5-fold increase in promoter activity, while a more modest 1.8-fold increase was measured with UVA (38.2 J/cm$^2$). In addition, in vitro studies revealed over a 30-fold increase in elastin promoter activity in response to UVB (5.5 mJ/cm$^2$), while no change was measured in response to UVA (2.2 J/cm$^2$). These results confirm the role of UVB in elastin promoter activation in photoaging and UVA as a contributing factor. In vitro results suggest a direct stimulatory effect of UV on the dermal fibroblasts, in addition to any contribution by pro-inflammatory cytokines from other inflammatory and resident cells of the dermis.

In the present invention, a transgenic mouse model has been developed which permits the investigation of human elastin promoter activity in response to ultraviolet irradiation both in vivo by direct irradiation of mouse skin, and in vitro by irradiation of dermal fibroblasts grown from skin explants. Previous studies investigating the effect of ultraviolet radiation on photoaging in animal models have measured elastic fiber damage, solar elastosis, skin wrinkling, and skin sagging. The similarity between the mouse and human action spectra for development of edema and erythema in response to ultraviolet radiation suggests that mouse models may accurately mimic human responses to ultraviolet radiation. For example, wrinkling of mouse skin mimics human wrinkling which occurs in chronically photodamaged skin. These changes take place more rapidly in mouse skin, permitting more rapid evaluation of ultraviolet radiation effects than may be possible in humans. However, differences in several parameters measured in previous studies are also apparent. For example, mice do not develop erythema in a manner similar to humans and the elastic fiber alterations in mice in response to ultraviolet radiation are qualitatively different from those occurring in chronically sun-damaged human skin. In addition, the numerous dermal cysts present in hairless mice proliferate in response to ultraviolet radiation, a response which has no clinical correlate in human skin. Skin sagging, a response in certain mice to high dose UVA, does not appear to have a histopathologic correlate in mice and may not have a clinical correlation to a human response. Finally, mouse skin is relatively thin in comparison to human skin, thus, permitting better penetration of ultraviolet radiation. This may, in part, account for the accentuated response of mouse skin to ultraviolet radiation. However, the decreased thickness of mouse skin may also exaggerate the potential effects of UVB as compared to UVA, relative to humans. UVB penetrates only the most superficial dermis in humans, whereas in mice, the relative proportion of the dermis exposed to UVB is much greater. Utilizing the human elastin promoter in the transgenic mouse model of the present, is believed to more accurately reflect the human response to ultraviolet radiation.

The approximate time of maximal promoter activation and the duration of promoter elevation after a single exposure of UVA or UVB radiation was determined. Mice were treated with a single dose of 245.7 mJ/cm$^2$ of UVB or 38.2 J/cm$^2$ of UVA. Elastin promoter activity, as measured by CAT assay, was maximal 24 hours after UVB exposure with a 4.6-fold increase over controls. CAT activity remained elevated 72 hours after irradiation at nearly 2 times control levels. By 96 hours, the activity fell to below one-third that of controls. After UVA irradiation, CAT activity was maximal 12–24 hours after light exposure, demonstrating a more modest increase of less than twice that of controls. This increase persisted until 48 hours after UVA exposure. By 72 hours after UVA exposure, CAT activity fell to one-third that of controls. To determine the earliest increase in CAT activity following UVB irradiation, mice were harvested 1, 2, 3 and 6 hours following UVB exposure. A 20% increase in CAT activity was measured 1 hour following exposure while a 70% elevation was measured 2 hours after exposure.

Since CAT activity decreases as a function of age, time course experiments underestimated relative CAT activity for time points after the initial 12 hour time point. Controls for time course experiments were harvested at the 12 hour time point. If the decrease in endogenous CAT activity is considered, CAT activity remained at, or near, maximal levels until 72 hours after light exposure for UVB-treated mice, and until 48 hours in UVA-treated mice. By 72 hours after UVA exposure and 96 hours after UVB exposure, CAT activity fell to one-third that of controls sacrificed 12 hours after light exposure. Untreated mice sacrificed 72 and 96 hours after 4–5 day old controls also demonstrated baseline CAT activity which was one-third that of the younger control mice. Thus, baseline endogenous CAT activity in mice 8–9 days old decreases to one-third that of 5 day old mice from the same litter.

The dose-response relationship for elastin promoter activity in UVB-treated mice was observed after only a single dose of UVB. Other in vivo models of photoaging require numerous treatments over a much longer period of time to demonstrate a measurable effect. Experimentally produced elastosis in mice was first produced by Sams et al. using very large amounts of ultraviolet radiation. *J. Invest. Dermatol.* 1964, 43:467–471. In these studies, one group of mice received 1,040 human minimal erythema doses (MEDs) over 3 months from a bank of fluorescent tubes, while another group received 13,000 MEDs given over 52 weeks in 260 treatments. Elastosis was demonstrated by histochemical staining for elastin and, in irradiated mice, demonstrated an increased elastin staining. Since this initial report, a number of researchers have used murine models of cutaneous photoaging evaluating the production of dermal elastosis. Sams et al., *J. Invest. Dermatol.* 1964, 43:467–471; Nakamura, K. and Johnson, W. C., *J. Invest. Dermatol.* 1968, 51:253–258; Berger et al., *Arch. Dermatol. Res.* 1980, 269:39–49; Kligman, L. H., *Arch. Dermatol. Res.* 1982, 272:229–238; Kligman et al., *J. Invest. Dermatol.* 1982, 78:181–189; Poulsen et al., *Br. J. Dermatol.* 1984, 110:531–538; Kligman et al., *J. Invest. Dermatol.* 1985, 84:272–276; Bissett et al., *Photochem. Photobiol.* 1987, 46:367–376; Bissett et al., *Photochem. Photobiol.* 1989, 50:763–769; Wulf et al., *Photodermatology* 1989, 6:44–51; Kligman, L. H. and Sayre, R. M., *Photochem. Photobiol.* 1991, 53:237–242; and Moran, M. and Granstein, R. D., *J. Invest. Dermatol.* 1994, 103:797–800. The number of treatments with ultraviolet radiation in these studies ranges from 36 to 260 given over 13 to 62 weeks. This is in contrast to the single doses used in the current study. Thus, the total dose of UVB used to produce measurable solar elastosis using the same UVB lamps in the present study, ranged from 6- (Bissett et al., *Photochem. Photobiol.* 1987, 46:367–376) to almost 40-fold (Poulsen et al., *Br. J. Dermatol.* 1984, 110:531–538) larger than the largest dose used with the model of the present invention.

The elevation of the elastin promoter in response to UVB and UVA was also determined to be dose dependent. Increasing doses of ultraviolet radiation were administered and skin harvested 24 hours after light exposure. In response to UVB irradiation at 30.7, 122.8 and 491.4 mJ/cm$^2$, CAT activity increased to 1.7-, 4.1- and 8.5-fold greater than controls, respectively. In response to UVA irradiation, a more modest increase in CAT activity was seen. Doses of 9.5 and 38.2 J/cm$^2$ resulted in increases of 1.6- and 1.7-fold over controls, respectively.

In addition to requiring substantially shorter treatment times and doses of ultraviolet radiation, the transgenic mouse model of the present invention yields quantitative data. With the exception of Kligman and Sayre, *Photochem. Photobiol.* 1991, 53:237–242, who used an image analysis system to quantify elastosis, the parameters used to assess degree of elastosis in the prior art were evaluated subjectively.

The effect of ultraviolet radiation on CAT activity in vitro was also determined. Early passage fibroblasts derived from skin explants of the transgenic mice were irradiated and harvested for determination of CAT activity 24 hours later. Doses of UVB ranged from 0.7 to 10.9 mJ/cm$^2$, with the highest doses resulting in over a 30-fold increase in CAT activity. Promoter activity, as measured by CAT assay, peaked at a dose of 5.5 mJ/cm$^2$, which corresponded with a treatment time of 40 seconds. CAT activity remained elevated at about 30-fold with increasing UVB doses, eventually resulting in a decrease in CAT activity which corresponds with cell death. In contrast, UVA doses of up to 2.2 J/cm$^2$, which corresponds with a light treatment time of over 18 minutes, did not increase CAT activity in vitro. Longer treatment times resulted in cell death.

The transgenic mouse model of the present invention provides a rapid, quantitative means of measuring human elastin promoter activity in response to single doses of ultraviolet radiation. Enhanced CAT activity was demonstrated in response to both UVA and UVB. Further, the ability to study the effects of ultraviolet radiation both in vivo and in vitro enables further investigation of the mechanisms responsible for elastin promoter activation by ultraviolet radiation. In addition, this model provides a tool for the rapid evaluation of sunscreens and other compounds thought to alter the effects of solar radiation.

Methods of identifying compounds capable of inhibiting cutaneous photodamage using the models of the present invention are also provided. In one embodiment a test compound is applied to the skin of a transgenic mouse capable of expressing human elastin promoter. The transgenic mouse is then exposed to ultraviolet radiation, either UVB or UVA and human elastin promoter activity in the mouse is determined. The human elastin promoter activity is then compared to that in transgenic mice also exposed to an equivalent dose of ultraviolet radiation which were not treated with the test compound to determine whether or not the test compound provided protection against the ultraviolet radiation. In another embodiment, fibroblast cells derived from a transgenic mouse capable of expressing human elastin promoter are treated with a test compound. The treated fibroblast cells are then exposed to UVB radiation and human elastin promoter activity in the fibroblast cells is determined. This activity is compared to fibroblast cells from the transgenic mice exposed to the same dose of UVB radiation but which were not treated with the test compound to determine if the test compound provided protection against the radiation.

The following nonlimiting examples are provided to further illustrate the present invention.

EXAMPLES

Example 1
Transgenic mice expressing the human elastin promoter

A homozygous line of transgenic mice expressing the 5.2-kb human elastin promoter linked to a CAT reporter gene was used. Hsu-Wong et al., *J. Biol. Chem.* 1994, 269:18072–18075. These mice express the human elastin promoter in a tissue-specific and developmentally regulated manner. Mice four or five days old were used since at this age, visible hair growth is not yet present.

Example 2
Fibroblast Cultures

Fibroblast cultures were established from the skin of transgenic mice by explanting tissue specimens onto the tissue culture plastic dishes and allowing cells to migrate to the surrounding area. The primary cultures were maintained in Dulbecco's modified Eagle's (DME) medium supplemented with 10% fetal calf serum, 1 mM L-glutamine and antibiotics at 37° C. The primary cell cultures were passaged by trypsinization and the subcultures in passages 2 or 3 were utilized for radiation experiments. After exposure to ultraviolet radiation, the cells were incubated in DME medium supplemented with 10% fetal calf serum for 24 hours, then harvested for determination of CAT activity as described in Example 3.

Example 3
CAT Assay

To measure the expression of the human elastin promoter/CAT reporter gene construct in the skin of transgenic mice and in fibroblast cultures established from these animals, CAT activity was determined. For extraction of the CAT from skin, the specimens were homogenized in 0.25 Tris-HCl, pH 7.5, using a tissue homogenizer (Brinkmann Instruments, Inc. Westbury, N.Y.). The homogenates were centrifuged at 10,000×g for 15 minutes at 4° C. and the protein concentration in the supernatant determined by a commercial protein assay kit (Bio-Rad Laboratories, Richmond, Calif.). Aliquots of the supernatant containing 100 µg of protein were used for assay of CAT activity by incubation with [$^{14}$C] chloramphenicol in accordance with well-known procedures. The acetylated and non-acetylated forms of radioactive chloramphenicol were separated by thin-layer chromatography and CAT activity was determined by the radioactivity in the acetylated forms as a percent of the total radioactivity in each sample.

Example 4
UV Sources

For administration of UVB radiation, a closely spaced array of seven Westinghouse FS-40 sunlamps was used which delivered uniform irradiation at a distance of 35 cm. Irradiating with UVA was performed using seven Sylvania FR40T12 PUVA lamps in the above mentioned array, filtered through window glass of 2 mm thickness to remove wavelengths below 320 nm. The energy output at 35 cm was measured with a Solar Light model 3D UVA and UVB detector (Solar Light Company, Philadelphia, Pa.). The output of FX-40 sunlamps was 23.4 units/hour of UVB at 38 cm, where each unit is equivalent to 21 mJ/cm$^2$ of erythema effective energy. The output for FR40T12 PUVA lamps filtered through window glass was 2.02 mW/cm$^2$, with no detectable UVB radiation.

Example 5
Irradiation

Mice were placed under the center of the light array and restrained with adhesive tape, exposing their dorsal surfaces to the ultraviolet radiation at a distance of 35 cm from the fluorescent tubes. Untreated control mice were restrained in a similar manner. To determine the time of maximal promoter activation and the duration of elevated promoter activity following UVA and UVB irradiation, time course experiments were carried out. Doses were selected in accordance with amounts showing moderate promoter activation. Mice were irradiated for one-half hour with UVB (dose of 245.7 mJ/cm$^2$) or with UVA for 5.2 hours (dose of 38.2 J/cm$^2$). Irradiated skin was then harvested over the next 72 to 96 hours for determination of CAT activity. Control mice were sacrificed at the first time point (12 hours after irradiation). To determine the earliest response of CAT activity to UVB irradiation, mice were harvested 1, 2, 3 and 6 hours after UVB exposure. Unirradiated mice were harvested 24, 48, 72 and 96 hours after control mice to determine the fall in endogenous CAT activity over time.

To determine the dose/response relationship for UVB, doses of 30.7, 122.8 and 491.4 mJ/cm$^2$ were administered over 0.06, 0.25 and 1 hours, respectively. The dose/response relationship for UVA was determined utilizing doses of 9.5 and 38.2 J/cm$^2$, administered over 1.3 and 5.2 hours, respectively. For each experiment, only mice from the same litter were used. Following light exposure, mice were returned to the mother for 24 hours and then sacrificed and skin harvested for determination of CAT activity. At least 2 mice were used for each dose or time point in each experiment.

Fibroblast cultures as described above were exposed for 5, 10, 20, 40 and 80 seconds of UVB corresponding to doses of 0.7, 1.4, 2.7, 5.5 and 10.9 mJ/cm$^2$, respectively. Cultures were exposed to UVA for 2.3, 4.6, 9.2 and 18.4 minutes corresponding to doses of 0.3, 0.6, 1.1 and 2.2 J/cm$^2$. To prevent light absorption by tissue culture medium, just prior to irradiation, tissue culture medium was removed from cells and replaced with a thin layer of phosphate buffered saline (PBS) sufficient to cover the cells. Control unirradiated cells were also placed in PBS. Medium was replaced in all dishes immediately after the last light dose was administered. Only fibroblasts from mice in the same litters were used for any given experiment and utilized in the first few passages. Two dishes of cells were used for each time point.

What is claimed is:

1. A method of identifying compounds capable of inhibiting cutaneous photodamage comprising:
   (a) applying a test compound to skin of a transgenic mouse capable of expressing a reporter gene regulated by a human elastin promoter;
   (b) exposing the transgenic mouse to UVB or UVA radiation; and
   (c) measuring expression of the reporter gene to determine human elastin promoter activity in the transgenic mouse.

2. A method of identifying compounds capable of inhibiting cutaneous photodamage comprising:

(a) contacting fibroblast cells derived from a transgenic mouse capable of expressing a reporter gene regulated by a human elastin promoter with a test compound;

(b) exposing the fibroblast cells to UVB radiation; and (c) measuring expression of the reporter gene to determine human elastin promoter activity in the fibroblast cells.

* * * * *